(12) United States Patent
Karuppiah et al.

(10) Patent No.: US 8,983,378 B2
(45) Date of Patent: Mar. 17, 2015

(54) METHOD AND SYSTEM FOR ENABLING A MOBILE DEVICE TO INTERFACE WITH A MEDICAL DEVICE

(75) Inventors: Saravanan Karuppiah, Tamilnadu (IN); Vishal Chaudhary, Tamil Nadu (IN); Venubabu Katragadda, Tamil Nadu (IN); Sankareswari Amudhasidhanandham, Tamil Nadu (IN)

(73) Assignee: HCL Technologies Limited, Chonnai, Tamil Nadu (IN)

( * ) Notice: Subject to any disclaimer, the term of this patent is extended or adjusted under 35 U.S.C. 154(b) by 239 days.

(21) Appl. No.: 13/557,944

(22) Filed: Jul. 25, 2012

(65) Prior Publication Data
US 2013/0210365 A1 Aug. 15, 2013

(30) Foreign Application Priority Data
Feb. 15, 2012 (IN) .............................. 566/CHE/2012

(51) Int. Cl.
*H04B 5/00* (2006.01)

(52) U.S. Cl.
USPC ......................... 455/41.1; 455/41.2; 455/63.1

(58) Field of Classification Search
USPC ............................... 455/41.1, 41.2, 63.1, 66.1
See application file for complete search history.

(56) References Cited

U.S. PATENT DOCUMENTS 8,588,687 B2 * 11/2013 Ramey et al. ................. 455/41.2
2011/0106191 A1 * 5/2011 Bennett et al. .................... 607/5

* cited by examiner

*Primary Examiner* — Tuan H Nguyen

(57) ABSTRACT

Mobile devices are used for several purposes other than just communication. Given herein are methods and systems for enabling a mobile device to interface with a medical device, mainly related to patient healthcare monitoring using the mobile device. The mobile can control or interface with a medical device in a deterministic manner through a mobile application. The mobile application module uses the available hardware resources of the mobile device to control or interface with a medical device. This enables the mobile device to fully control or interface with the medical device without any external or internal disturbance.

17 Claims, 5 Drawing Sheets

METHOD AND SYSTEM FOR ENABLING A MOBILE DEVICE TO INTERFACE WITH A MEDICAL DEVICE

The present application is based on, and claims priority from, IN Application Number 556/CHE/2012, filed on 15 Feb. 2012, the disclosure of which is hereby incorporated by reference herein.

TECHNICAL FIELD

The embodiments herein relate to healthcare and, more particularly, to use of a mobile device in healthcare.

BACKGROUND

In the information centric world, patient's health care is to be monitored on a continuous basis. This is of prime importance since the information about the patient helps the physician to give further treatment to the patient.

Handheld devices (such as mobile phones, smart phones, tablets, PDAs, dedicated devices) have been used in conjunction with medical devices. However, use of such devices have been only in the diagnostic mode, with the device receiving information from the medical device and the handheld device performing analysis on the data and providing an analysis and report (which may be diagnostic in nature).

Handheld devices are unable to control the medical devices as the timing requirement of time critical operation cannot be guaranteed. For example calls can come when an interaction is ongoing between the mobile device and the medical device. Due to aforementioned reasons, there is need for a system to behave in a deterministic way in a mobile device to control or interface with the medical device.

SUMMARY

In view of the foregoing, an embodiment herein provides a mobile device comprising at least one means configured for enabling the mobile device to communicate with at least one medical device, on a user of the mobile device providing an input.

Also, provided herein is a medical device comprising at least one means configured for enabling a mobile device to communicate with the medical device.

Disclosed herein is a method for enabling a mobile device to communicate with a medical device, the method comprising of the mobile device initiating communication with the medical device, on a user of the mobile device providing an input; the medical device accepting inputs from the mobile device; and the medical device performing tasks based on the inputs from the mobile device.

These and other aspects of the embodiments herein will be better appreciated and understood when considered in conjunction with the following description and the accompanying drawings.

BRIEF DESCRIPTION OF THE FIGURES

The embodiments herein will be better understood from the following detailed description with reference to the drawings, in which.

DETAILED DESCRIPTION OF EMBODIMENTS

Figure 1:
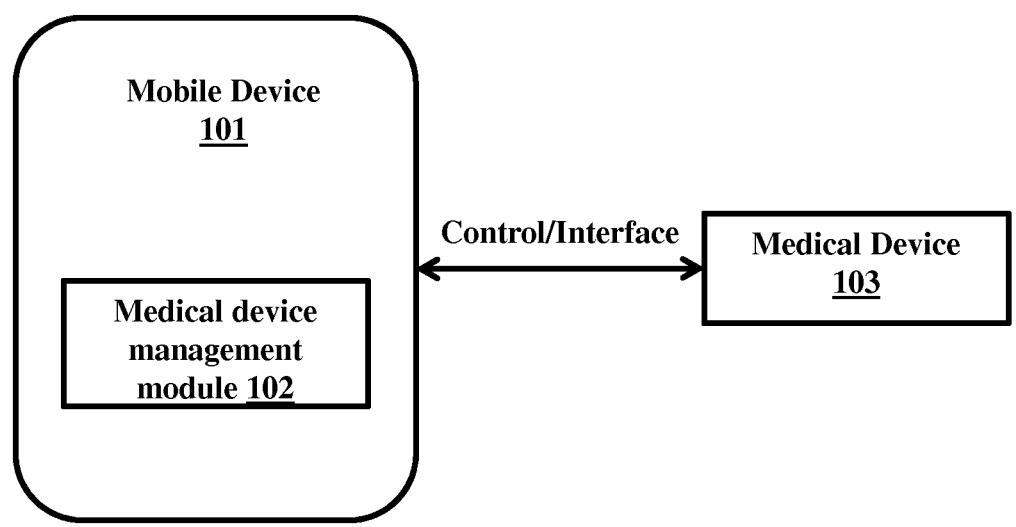
FIG. 1 illustrates a general block diagram of the mobile device that control or interface with the medical device, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein disclose a method and system for a mobile device to control or interface with a medical device in a deterministic manner. Referring now to the drawings, and more particularly to FIGS. 1 through 5, where similar reference characters denote corresponding features consistently throughout the figures, there are shown embodiments.

A mobile application module resides in the mobile device to control or interface with a connected medical device is disclosed. The mobile application module uses the hardware resources of the mobile device to control or interface with the medical device. This enables the mobile device to fully control or interface with the medical device without any disturbance.

In an embodiment herein, the mobile device referred to throughout the application may be a mobile phone, smart phone, PDA, tablet and so on.

In an embodiment herein, the medical device referred to throughout the application may be but not be restricted to Implantable pump, Blood glucose monitors, Insulin pump, Pace makers or any other medical device related to medical applications like diagnosis, therapy or surgery.

In an embodiment herein the medical device may be implanted in the patient body or may be attached to the patient skin and interface with the mobile device in any of the wired or wireless communication.

FIG. 1 illustrates a general block diagram of the mobile device that controls or interfaces with the medical device, according to embodiments as disclosed herein. As depicted in the block diagram, the mobile device 101 comprises of a medical device management module 102, wherein the medical device management module 102 controls or interfaces with the medical device 103 via the mobile device 101. The mobile device 101 may interface with the medical device 103 using a suitable connection means. The suitable connection means may be a wired connection means or a wireless connection means.

Figure 2:
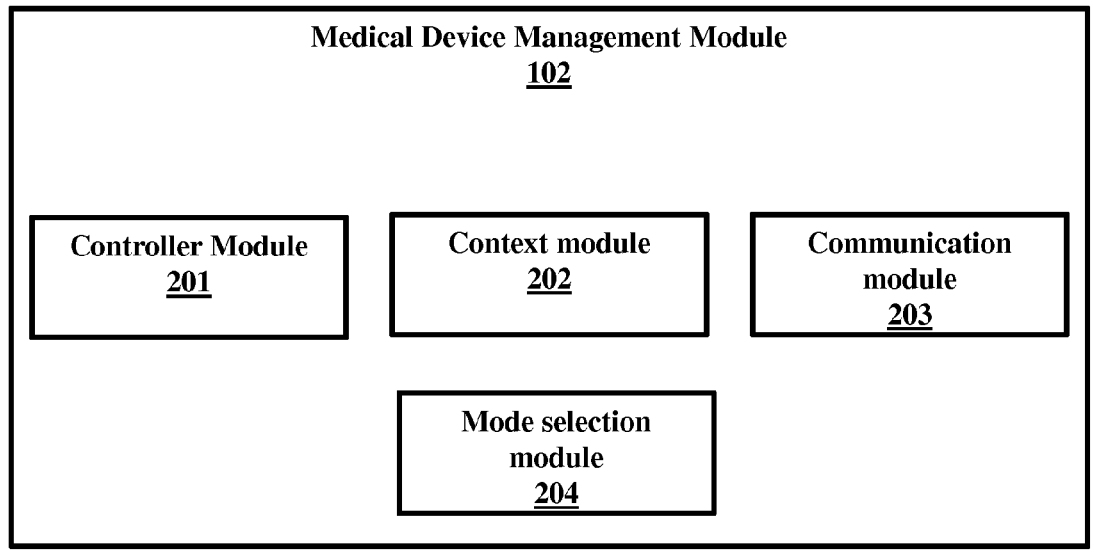
FIG. 2 is a general block diagram of the Medical Device Management Module, according to embodiments as disclosed herein.

FIG. 2 is a general block diagram of the Medical Device Management Module, according to embodiments as disclosed herein. The medical device management module 102 comprises of a plurality of modules which enables the user of the mobile device 101 to efficiently control and interface with the medical device 103. The medical device management module 102 comprises of a controller module 201, a context module 202, a communication module 203 and a mode selection module 204.

When the mobile device 101 controls the medical device 103, the controller module 201 enables the medical device management module 102 to access all the hardware resources of the mobile device 101 required to control the medical device 103. The controller module 201 controls all other modules in the medical device management module 102. The controller module 201 may control several prominent features in the mobile device such as media and entertainment services, radio, incoming and outgoing calls, SMS and other time consuming applications and so on. In one embodiment, the controller module 201 controls the time consuming feature such as Anti-Virus.

The context module 202 looks at the context of the management module 102 and the medical device 103 and based on that enables/disables features of the management module 102 and/or the mobile device 101, when the mobile device 101 interfaces with the medical device 103. In an embodiment herein, the context module 202 allows a call from a care giver to get displayed when the medical application interface with the medical device.

The communication module 203 enables communication between the mobile device 101 and the medical device 103. The communication module 203 may communicate with the medical device using a suitable communication means. The suitable communication means may be a wired means (such as a USB cable, WLAN cable and any other means which enables two devices to communicate with each other) or a wireless means (such as Bluetooth, Zigbee, NFC, WiFi and any other means which enables two devices to communicate with each other).

The mode selection module 204 enables the user of the mobile device 101 to select one of the available modes such as medical mode and normal mode. The medical mode may be selected through an option such as a key combination entry or display selection or a combination of both in the mobile device when the mobile device 101 is in normal mode.

In another embodiment, the mode selection module 204 may enable the user to select the medical mode during the boot-up operation of the mobile device 101. During the boot-up operation, the mode selection module 204 may display a plurality of options such as medical mode and normal mode using the display of the mobile device 101.

In yet another embodiment, the mode selection module 204 may enable the user to select the medical mode by means of activating the medical application in the mobile device.

Figure 3:
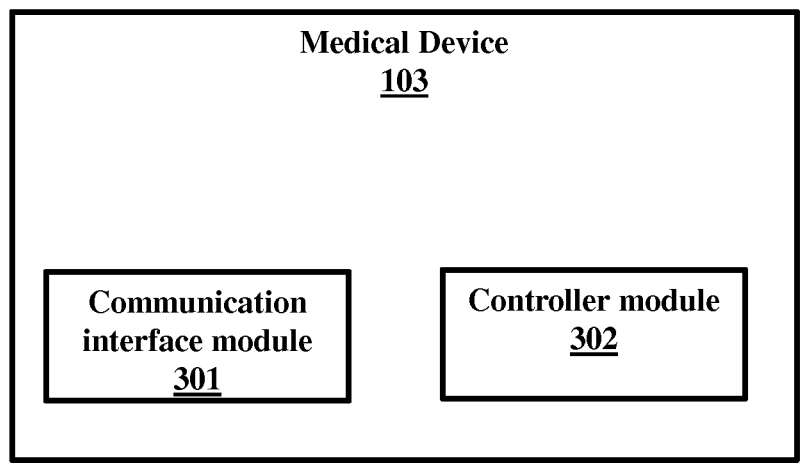
FIG. 3 is a general block diagram of the medical device, according to embodiments as disclosed herein.

FIG. 3 is a general block diagram of the medical device, according to embodiments as disclosed herein. The medical device 103 comprises of a communication interface module 301 and a controller module 302.

The communication interface module 301 enables the interface between the mobile device 101 and medical device 103. The patient information is communicated to the mobile device using this communication interface module 301. The medical device 103 controlling information from mobile device 101 is communicated to the medical device 103 using this communication interface module 301. The communication interface module 301 may communicate with the mobile device using a suitable communication means. The suitable communication means may be a wired means (such as a USB cable, WLAN cable and any other means which enables two devices to communicate with each other) or a wireless means (such as Bluetooth, Zigbee, NFC, WiFi and any other means which enables two devices to communicate with each other).

The controller module 302 enables the operation of the medical device 103, according to the instructions received from the mobile device 101, via the communication interface module 301. The controller module 302 may also receive inputs from other means other than the mobile device 101, such as the user interface of the medical device 103. The controller module 302 may be configured to send the information to the mobile device 101 in a continuous manner or at pre-configured specific intervals. The controller module 302 may also send the mobile device 101 only specific information, as specified by the user of the mobile device 101.

Figure 4:
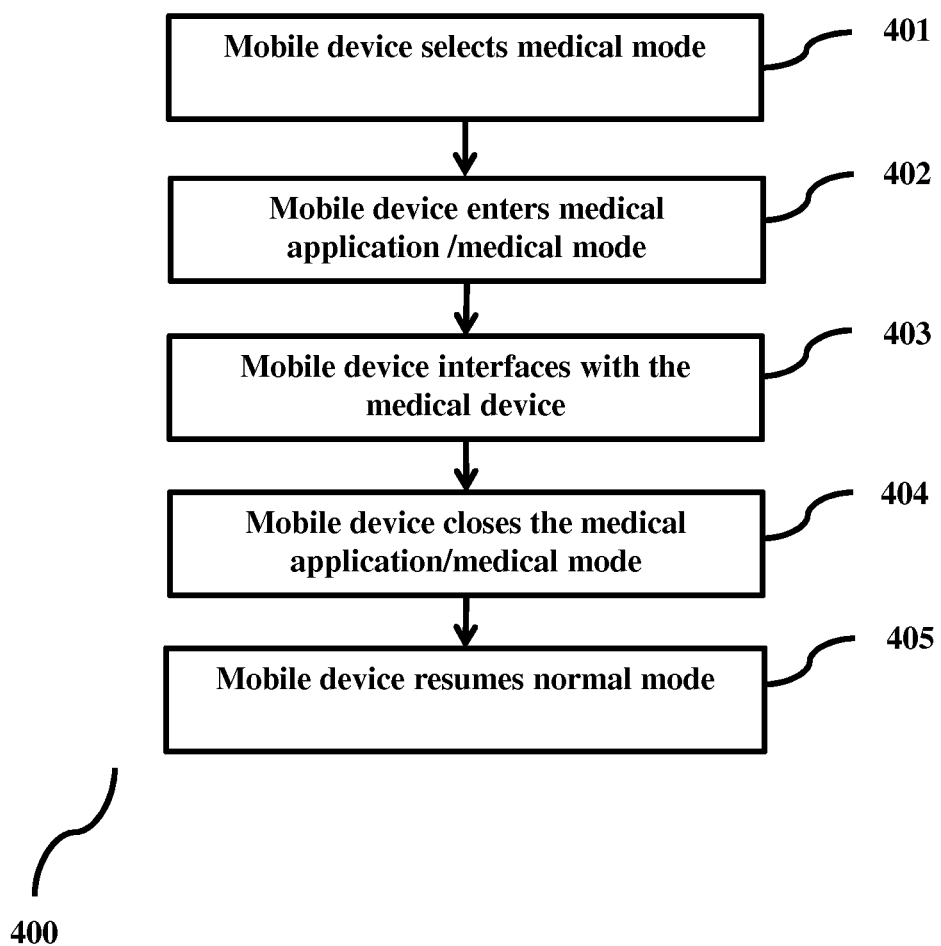
FIG. 4 is a flow chart illustrating the system that performs the control or interface operation with the medical device in normal mode, according to embodiments as disclosed herein.

FIG. 4 is a flow chart illustrating the system that performs control or interface operation with the medical device in normal mode, according to embodiments as disclosed herein. The flow chart depicts (400) the selection of medical mode when the mobile device works in normal mode. The mobile device when working in a normal mode works like a normal device and supports all features as per the device specifications. Now, the mobile device selects (401) medical mode of operation. This may be done by the user selecting an option available on the mobile device 101 using the menu and/or pressing at least one key of the mobile device 101.

Further, in some embodiments, this may be done by selecting the medical application in the mobile device 101. The mobile device enters (402) medical mode. The mobile device 101 may shut down other features of the mobile device 101, such as making and receiving calls, receiving/sending messages (SMSs, emails, MMSs and so on), multimedia options and any other feature which may interfere with the operation of the medical device 103. The mobile device 101 may enable specific features depending on instructions from the user or needs of the medical application. Then the mobile device interfaces (403) with the medical device by any of the suitable interfacing means. After receiving inputs from the user (using the menu and/or pressing at least one key of the mobile device 101), the mobile device closes (404) the medical mode and the medical application terminates the communication with the medical device and resumes (405) the normal mode and works like a normal device. The various actions in system 400 may be performed in the order presented, in a different order or simultaneously. Further, in some embodiments, some actions listed in FIG. 4 may be omitted.

Figure 5:
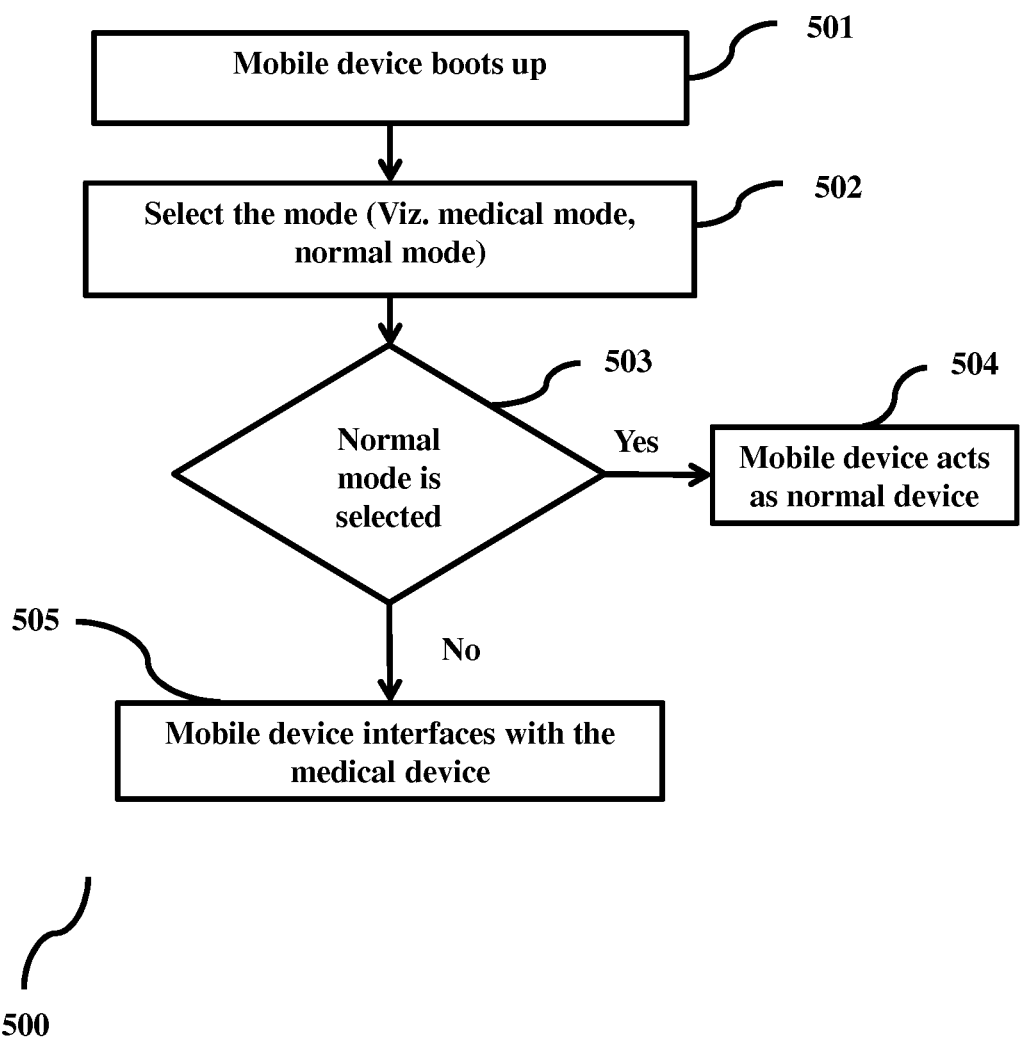
FIG. 5 is a flow chart illustrating the system that performs the control or interface operation with the medical device enabled during boot-up operation of the mobile device, according to embodiments as disclosed herein.

FIG. 5 is a flow chart illustrating the system that performs control or interface operation with the medical device enabled during boot-up operation of the mobile device, according to embodiments as disclosed herein. The flowchart shows (500) a system in which the medical mode is selected during the boot-up operation of the mobile device. When mobile device boots up (501), the user is presented with options related to the mode to be selected. On the user selecting (502) a mode, the mobile device 101 checks (503) whether normal mode is selected. If the systems identifies that the normal mode is selected then the mobile device acts (504) as a normal device and supports all features as per the device specifications. When the mobile device 101 identifies (505) that the normal mode is not selected and the medical mode is selected then the mobile device 101 enters medical mode. The mobile device 101 may shut down other features of the mobile device 101, such as making and receiving calls, receiving/sending messages (SMSs, emails, MMSs and so on), multimedia options and any other feature which may interfere with the operation of the medical device 103. The mobile device 101 may enable specific features depending on instructions from the user or needs of the medical application. By selecting the medical mode, the mobile device is fully utilized for medical applications such as receiving the patient health information from the medical device. The various actions in system 500 may be performed in the order presented, in a different order or simultaneously. Further, in some embodiments, some actions listed in FIG. 5 may be omitted.

In one embodiment, the system virtualizes a medical device on a standard handheld platform by sandboxing the medical mode to avoid interference from external sources or features available on the mobile device such as SMS, GPRS, and Anti-virus that may potentially interrupt or disrupt or impact performance when the mobile device is being used for medical purpose.

The system uses a standard mobile device connected to a medical device. In one embodiment it is also connected to an automated clinical decision system or with built in rules on the mobile device itself with mechanism to notify physician or even people in the network of the patient. This enables to monitor the patient even when patient moves around different locations and reduces burden on care givers as they are notified only when exceptions occur.

In one embodiment, the system uses a new medical application, in this case only the application level program code needs to be designed or developed and validated since the base frame work like hardware and software is already available.

This system mentioned in the application enables the patients to get discharged from hospital quickly as the patient can be monitored or treated remotely from his home through the medical application in the mobile device.

The embodiments disclosed herein can be implemented through at least one software program running on at least one hardware device and performing network management functions to control the network elements. The network elements shown in FIGS. 1-3 include blocks which can be at least one of a hardware device, or a combination of hardware device and software module.

The embodiment disclosed herein specifies a system for monitoring the patient health information. The mechanism allows the mobile device to control and interface with the medical device providing a system thereof. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in a preferred embodiment through or together with a software program written in e.g. Very high speed integrated circuit Hardware Description Language (VHDL) another programming language, or implemented by one or more VHDL or several software modules being executed on at least one hardware device. The hardware device can be any kind of device which can be programmed including e.g. any kind of computer like a server or a personal computer, or the like, or any combination thereof, e.g. one processor and two FPGAs. The device may also include means which could be e.g. hardware means like e.g. an ASIC, or a combination of hardware and software means, e.g. an ASIC and an FPGA, or at least one microprocessor and at least one memory with software modules located therein. Thus, the means are at least one hardware means and/or at least one software means. The method embodiments described herein could be implemented in pure hardware or partly in hardware and partly in software. The device may also include only software means. Alternatively, the application may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims as described herein.

We claim:
1. A mobile device configured to enable communication with at least one medical device, said mobile device comprising:
    at least a medical device management module, wherein said medical device management module comprises,
        a controller module configured to control functions of at least one of the medical device management module and the mobile device;
        a context module configured to at least one of enable and disable features of at least one of the medical device management module and the mobile device, based on a context of at least one of the medical device management module, the mobile device and the medical device;
        a communication module configured to enable communication between the mobile device and the medical device; and
        a mode selection module configured to enable a user of the mobile device to select at least one of a normal mode and a medical mode, wherein said medical mode is configured to be activated by at least one of,
            a combination of keys present in said mobile device;
            a display selection on said mobile device;
            a combination of keys present in said mobile device and a display selection on said mobile device;
            an option selected during boot up of said mobile device; and
            an option for a medical application present in menu of said mobile device.

2. The mobile device as claimed in claim 1, wherein said mobile device further comprises a means for avoiding interference from at least one of external sources and from features present on said mobile device.

3. The mobile device as claimed in claim 2, wherein the mobile device is configured to virtualize the medical device on a standard handheld platform by sandboxing the medical mode.

4. The mobile device as claimed in claim 1, wherein said mobile device, upon the selection of the normal mode, is configured to close the medical mode and resume the normal mode.

5. The mobile device as claimed in claim 1, wherein said mobile device, upon the selection of the medical mode, is configured to close the normal mode and resume the medical mode.

6. The mobile device as claimed in claim 1, wherein the mobile device is configured to perform at least one of a control, an interface and a mode selection during a boot-up operation of the mobile device.

7. A mobile device configured to enable communication with at least one medical device, said mobile device comprising:
- at least a medical device management module, wherein said medical device management module comprises,
  - a controller module configured to control functions of at least one of the medical device management module and the mobile device;
  - a context module configured to at least one of enable and disable features of at least one of the medical device management module and the mobile device, based on a context of at least one of the medical device management module, the mobile device and the medical device;
  - a communication module configured to enable communication between the mobile device and the medical device; and
  - a mode selection module configured to enable a user of the mobile device to select at least one of a normal mode and a medical mode, wherein said medical mode is configured to be activated by at least one of,
    - a combination of keys present in said mobile device;
    - a display selection on said mobile device;
    - a combination of keys present in said mobile device and a display selection on said mobile device;
    - an option selected during boot up of said mobile device; and
    - an option for a medical application present in menu of said mobile device;
- further wherein said medical device comprises,
  - a communication interface module configured to enable at least interlace between the mobile device and the medical device, wherein said communication contains at least instructions received from the mobile device to the medical device; and
  - a controller module configured to at least one of,
    - enable at least operation of the medical device in accordance with the instructions received from the mobile device;
    - receive inputs from means other than the mobile device; and
    - send information to the mobile device in at least one of a continuous manner and at pre-configured intervals.

8. A method for enabling a mobile device to communicate with a medical device, said method comprising:
- selecting at least one of a normal mode and a medical mode, wherein said medical mode is configured to be activated by at least one of,
  - a combination of keys present in said mobile device;
  - a display selection on said mobile device;
  - a combination of keys present in said mobile device and a display selection on said mobile device;
  - an option selected during boot up of said mobile device; and
  - an option for a medical application present in menu of said mobile device;
- initiating communication with said medical device by said mobile device, wherein said communication is initiated upon input being received by said mobile device via a communication module present within said mobile device;
- accepting inputs from said mobile device by said medical device via a communication interface module present within said medical device; and
- performing tasks based on said inputs from said mobile device, by a controller module present within said medical device.

9. The method as claimed in claim 8, said method comprising of said mobile device avoids interference from at least one of external sources and from features present on said mobile device.

10. The method as claimed in claim 9, wherein the mobile device is configured to virtualize the medical device on a standard handheld platform by sandboxing the medical mode.

11. The method as claimed in claim 8, wherein said mobile device, upon the selection of the normal mode, is configured to close the medical mode and resume the normal mode.

12. The method as claimed in claim 8, wherein said mobile device, upon the selection of the medical mode, is configured to close the normal mode and resume the medical mode.

13. The method as claimed in claim 8, wherein the mobile device is configured to perform at least one of a control, an interface and a mode selection during a boot-up operation of the mobile device.

14. A mobile device configured to enable communication with at least one medical device, said mobile device comprising:
- at least a medical device management module, wherein said medical device management module comprises,
  - a controller module configured to control functions of at least one of the medical device management module and the mobile device;
  - a context module configured to at least one of enable and disable features of at least one of the medical device Management module and the mobile device, based on a context of at least one of the medical device management module, the mobile device and the medical device;
  - a communication module configured to enable communication between the mobile device and the medical device; and
  - a mode selection module configured to enable a user of the mobile device to select at least one of a normal mode and a medical mode, wherein said medical mode is configured to he activated by at least one of,
    - a combination of keys present in said mobile device;
    - a display selection on said mobile device;
    - a combination of keys present in said mobile device and a display selection on said mobile device;
    - an option selected during hoot up of said mobile device; and
    - an option for a medical application present in menu of said mobile device,
- wherein the mobile device is in communication with at least an automated clinical decision system, further wherein the automated clinical decision system enables monitoring of at least a patient and notification upon occurrence of exceptions.

15. A mobile device configured to enable communication with at least one medical device, said mobile device comprising:
- at least a medical device management module, wherein said medical device management module comprises,
  - a controller module configured to control functions of at least one of the medical device management module and the mobile device;
  - a context module configured to at least one of enable and disable features of at least one of the medical device management module and the mobile device, based on a context of at least one of the medical device management module, the mobile device and the medical device;
a communication module configured to enable communication between the mobile device and the medical device; and
a mode selection module configured to enable a user of the mobile device to select at least one of a normal mode and a medical mode, wherein said medical mode is configured to he activated by at least one of,
a combination of keys present in said mobile device;
a display selection on said mobile device;
a combination of keys present in said mobile device and a display selection on said mobile device;
an option selected during boot up of said mobile device; and
an option for a medical application present in menu of said mobile device,
wherein the mobile device is in communication with at least an automated clinical decision system, further wherein the automated clinical decision system enables monitoring of at least a patient and notification upon occurrence of exceptions.

16. A mobile device configured to enable communication with at least one medical device, said mobile device comprising:
at least a medical device management module, wherein said medical device management module comprises,
a controller module configured to control functions of at least one of the medical device management module and the mobile device;
a context module configured to at least one of enable and disable features of at least one of the medical device management module and the mobile device, based on a context of at least one of the medical device management module, the mobile device and the medical device;
a communication module configured to enable communication between the mobile device and the medical device; and
a mode selection module configured to enable a user of the mobile device to select at least one of a normal mode and a medical mode, wherein said medical mode is configured to he activated by at least one of,
a combination of keys present in said mobile device;
a display selection on said mobile device;
a combination of keys present in said mobile device and a display selection on said mobile device;
an option selected during boot up of said mobile device; and
an option for a medical application present in menu of said mobile device,
wherein the mobile device is configured to contain built-in rules, said rules configured to enable monitoring of at least a patient and notification upon occurrence of exceptions.

17. A mobile device configured to enable communication with at least one medical device, said mobile device comprising:
at least a medical device management module wherein said medical device management module comprises,
a controller module configured to control functions of at least one of the medical device management module and the mobile device;
a context module configured to at least one of enable and disable features of at least one of the medical device management module and the mobile device, based on a context of at least one of the medical device management module, the mobile device and the medical device;
a communication module configured to enable communication between the mobile device and the medical device; and
a mode selection module configured to enable a user of the mobile device to select at least one of a normal mode and a medical mode wherein said medical mode is configured to he activated by at least one of,
a combination of keys present in said mobile device;
a display selection on said mobile device;
a combination of keys present in said mobile device and a display selection cm said mobile device;
an option selected during boot up of said mobile device; and
an option for a medical application present in menu or said mobile device,
wherein the mobile device is configured to contain built-in rules, said rules configured to enable monitoring of at least a patient and notification upon occurrence of exceptions.

* * * * *